United States Patent
Van Der Waal et al.

(10) Patent No.: US 10,131,600 B2
(45) Date of Patent: *Nov. 20, 2018

(54) PROCESS FOR PREPARING ETHYLENE GLYCOL FROM A CARBOHYDRATE

(71) Applicant: AVANTIUM KNOWLEDGE CENTRE B.V., Amsterdam (NL)

(72) Inventors: Jan Cornelis Van Der Waal, Amsterdam (NL); Gerardus Johannes Maria Gruter, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/543,064

(22) PCT Filed: Jan. 13, 2016

(86) PCT No.: PCT/NL2016/050026
§ 371 (c)(1),
(2) Date: Jul. 12, 2017

(87) PCT Pub. No.: WO2016/114658
PCT Pub. Date: Jul. 21, 2016

(65) Prior Publication Data
US 2018/0002258 A1    Jan. 4, 2018

(30) Foreign Application Priority Data

Jan. 13, 2015  (NL) .................... 2014117

(51) Int. Cl.
C07C 29/74    (2006.01)
B01J 21/00    (2006.01)
B01J 23/00    (2006.01)
C07C 29/132   (2006.01)
B01J 21/18    (2006.01)
B01J 23/30    (2006.01)
B01J 23/46    (2006.01)
B01J 35/00    (2006.01)

(52) U.S. Cl.
CPC ............ C07C 29/132 (2013.01); B01J 21/18 (2013.01); B01J 23/30 (2013.01); B01J 23/462 (2013.01); B01J 35/0006 (2013.01); C07C 29/74 (2013.01); Y02P 20/52 (2015.11)

(58) Field of Classification Search
CPC ........ C07C 29/74; C07C 29/132; B01J 21/18; B01J 23/33
USPC ....................................... 568/863
See application file for complete search history.

(56) References Cited

U.S. PATENT DOCUMENTS

| | | | |
|---|---|---|---|
| 2,360,685 A | 10/1944 | Jensen | |
| 4,430,253 A | 2/1984 | Dubeck et al. | |
| 5,425,853 A | 6/1995 | Berg | |
| 6,620,292 B2 | 9/2003 | Wingerson | |
| 8,222,464 B2 * | 7/2012 | Kalnes | C07C 29/132 568/852 |
| 2011/0313208 A1 | 12/2011 | Kalnes et al. | |
| 2011/0313209 A1 | 12/2011 | Kalnes et al. | |
| 2012/0172633 A1 | 7/2012 | Zhang | |
| 2017/0362146 A1 | 12/2017 | Van Der Waal | |

FOREIGN PATENT DOCUMENTS

| | | |
|---|---|---|
| CN | 101768050 A | 7/2010 |
| CN | 102643165 A | 8/2012 |
| CN | 102731255 A | 10/2012 |
| CN | 103420797 A | 12/2013 |
| WO | 20130015955 A2 | 1/2013 |
| WO | 20140173973 A1 | 10/2014 |
| WO | 2016114658 A1 | 7/2016 |
| WO | 2016114659 A1 | 7/2016 |
| WO | 2016114660 A1 | 7/2016 |

OTHER PUBLICATIONS

International Search Report of Application No. PCT/NL2016/050026 dated Jun. 6, 2016.
Ji, N. et al., "Catalytic conversion of cellulose into ethylene glycol over supported carbide catalysts", Catalysis Today, Sep. 30, 2009, pp. 77-85, vol. 147, No. 2, Elsevier, NL.
International Search Report of Application No. PCT/NL2016/050028 dated Jun. 6, 2016.
Zhao et al., Guanhong et al., "Catalytic Conversion of Concentrated Glucose to Ethylene Glycol with Semicontinuous Reaction System", Ind. Eng. Chem. Res., USA, 2013, vol. 52, pp. 9566-9572.

* cited by examiner

Primary Examiner — Sikarl A Witherspoon
(74) Attorney, Agent, or Firm — Thomas|Horstemeyer, LLP

(57) ABSTRACT

Ethylene glycol is prepared from a carbohydrate source in a process,
wherein hydrogen, the carbohydrate source, a liquid diluent and a catalyst system are introduced as reactants into a reaction zone;
wherein the catalyst system comprises a tungsten compound and at least one hydrogenolysis metal selected from the groups 8, 9 or 10 of the Periodic Table of the Elements;
wherein the diluent that is introduced into the reaction zone comprises an alkylene glycol; and
wherein the carbohydrate source is reacted with hydrogen in the presence of the catalyst system to yield an ethylene glycol-containing product.

25 Claims, No Drawings

PROCESS FOR PREPARING ETHYLENE GLYCOL FROM A CARBOHYDRATE

CROSS-REFERENCE TO RELATED APPLICATION

This application is the National Stage of International Application No. PCT/NL2016/050026, filed 13 Jan. 2016, which claims the benefit of and priority to NL Application No. 2014117, having the title "Process For Preparing Ethylene Glycol From A Carbohydrate," filed on 13 Jan. 2015, the entire disclosures of which are incorporated by reference in their entireties as if fully set forth herein.

TECHNICAL FIELD

The present invention relates to a process for the preparation of ethylene glycol from a carbohydrate source. In particular it relates to a process for preparing ethylene glycol from a sustainable carbohydrate resource using a specific catalyst system.

BACKGROUND

The catalytic conversion of carbohydrates from a sustainable resource to valuable chemicals such as alkylene glycols has gained interest. Alkylene glycols are interesting chemicals that find application in the preparation of polyesters, such as poly(alkylene terephthalate), poly(alkylene naphthenate) or poly(alkylene furandicarboxylate). Further applications of alkylene glycols, in particular ethylene glycol, include its use as anti-freeze. By enabling the preparation of such chemicals from sustainable resources, the dependence of fossil fuel resources is reduced. Since there is a desire to reduce the dependence of fossil fuels there is a growing need for different sustainable resources for the production of alkylene glycols such as ethylene glycol.

In U.S. Pat. No. 7,960,594 a process is described wherein ethylene glycol is produced from cellulose. This process involves catalytic degradation and hydrogenation reactions under hydrothermal conditions. More in particular, the process is carried out by contacting cellulose at elevated temperature and pressure with a catalyst system comprising two sorts of active components in the presence of hydrogen. The first active component comprises tungsten or molybdenum in its metallic state or its carbide, nitride or phosphide. The second component is selected from the hydrogenation metals from Groups 8, 9 and 10 of the Periodic Table of Elements, and includes cobalt, nickel, ruthenium, rhodium, palladium, iridium and platinum. In experiments the compounds were used on a carrier, such as activated carbon. Moreover, it appears that the reaction conditions that results in satisfactory yields include a temperature of 220-250° C. and a hydrogen pressure of 3 to 7 MPa (measured at room temperature). When a 1% wt slurry of cellulose is subjected to these compounds for 30 minutes, ethylene glycol is obtained in yields of up to 69%. However, it also appears that when the reaction is continued for a prolonged period the ethylene glycol yield reduces.

In U.S. Pat. No. 8,410,319 a continuous process is described wherein a cellulose-containing feedstock is contacted with water, hydrogen and a catalyst to generate at least one alkylene glycol. The catalyst comprises a first metal component selected from the group consisting of Mo, W, V, Ni, Co, Fe, Ta, Nb, Ti, Cr, Zr and combinations thereof. The first metal component is in the elemental state or the metal is the carbide, nitride or phosphide compound. The catalyst further comprises Pt, Pd, Ru and combinations thereof, wherein the metal is in the elemental state. The catalyst components are comprised on a carrier.

This reaction has been further studied on catalyst systems that contain nickel and tungsten on a carrier. There it has been found that nickel and tungsten are leached into the solution during the reaction, which accounts for the gradual deterioration of the catalyst performance (cf. Na Ji et al., ChemSusChem, 2012, 5, 939-944). The leaching of tungsten and other metals has been confirmed in the study reported in M. Zheng et al., Chin. J. Catal., 35 (2014) 602-613. The latter document also discloses that in addition to ethylene glycol different by-products are obtained, including 1,2-propylene glycol, erythritol, glycerol, mannitol and sorbitol.

US 2011/0312488 describes a catalyst system for the generation of alkylene glycols from a carbohydrate as a potential alternative for a catalyst containing the metal components in the elemental state; this catalyst system comprises at least one metal with an oxidation state of at least +2. More in particular this US application discloses a catalyst system comprising a first metal component with an oxidation state of at least +2 and a hydrogenation component. The hydrogenation component can be selected from a wide range of metals in any oxidation state, including in the elemental state. The hydrogenation component may in particular comprise an active metal component selected from the group consisting of Pt, Pd, Ru, Rh, Ni, Ir and combinations thereof. The first metal component may also be selected from a range of metals, but in particular the compounds comprising the first metal component may be selected from the group comprising tungstic acid, molybdic acid, ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxides, heteropoly compounds of tungsten and various salts and oxides of molybdenum, niobium, vanadium, zirconium, titanium and chromium. The catalyst system according to US 2011/0312488 is stated to improve the selectivity to ethylene glycol and propylene glycol, with a reduced production of butane diols. The ethylene glycol generation is shown in some experiments, indicating that ammonium metatungstate is the preferred first metal component and that as preferred hydrogenation component platinum and nickel may be used. The use of nickel-containing catalyst systems results in the highest yields of ethylene glycol and optionally propylene glycol.

In the above-mentioned article of M. Zheng et al., Chin. J. Catal., 35 (2014) 602-613, the conclusion is drawn that tungsten acid-based catalysts are the most promising candidates for future commercialization of the cellulose-to-ethylene-glycol process. A hydrogenation component is added to such tungsten acid-based catalysts. Examples include ruthenium on activated carbon, but Raney nickel is considered the most promising candidate for commercialization.

The conversion of a carbohydrate to alkylene glycol involves complex reactions. It has been shown in M. Zheng et al., Chin. J. Catal., 35 (2014) 602-613, that lower concentrations of carbohydrate and high reaction temperatures, i.e. above 200° C., are beneficial to ethylene glycol production. This appears to be confirmed in WO 2014/161852, containing experiments wherein glucose solutions with increasing glucose concentrations, ranging from 1% wt to 6% wt, were contacted with hydrogen in the presence of a catalyst system comprising tungsten and ruthenium. The higher the glucose concentration was, the lower the yield of ethylene glycol became. In order to remedy this disadvantageous effect, it is proposed in WO 2014/161852 to contact a first small portion of the carbohydrate with hydrogen and the catalyst in a solution with a carbohydrate concentration of less than 2% wt, and only when the first portion has reacted, to add further portions of the carbohydrate. In this respect the process is similar to the semi-continuous reactions described in G. Zhao et al., Ind. Eng. Chem. Res., 2013, 52, 9566-9572. Both WO 2014/161852 and G. Zhao et al. in Ind. Eng. Chem. Res., 2013, 52, 9566-9572, mention that, in addition to ethylene glycol, 1,2-butane diol (butylene glycol) is produced. The relative amount of butylene glycol can be in the order of 10%, based on the yield of ethylene glycol. Since butylene glycol and ethylene glycol form an azeotrope, it is difficult to separate the compounds easily via distillation.

As indicated above, alkylene glycols find application in a range of products. An important application is its use as monomer in the production of polyesters. Especially when alkylene glycols, such as ethylene glycol, are used in the production of polyesters, the alkylene glycol must be pure. As shown in e.g. WO 2014/161852, the conversion of hexose-containing carbohydrates, such as glucose and cellulose yields a mixture of ethylene glycol, propylene glycol and some butylene glycol.

The yields of ethylene glycol in the process according to WO 2014/161852 are in the order of 22 to about 40%, based on the amount of glucose used as starting material. In addition to other alkylene glycols, such as propylene glycol and butylene glycol, several other by-products are thus formed.

SUMMARY

Therefore there is a desire to increase the yield of ethylene glycol, and to reduce the amount of by-products formed. It has now surprisingly been found that when the reaction starts from the beginning in a diluent that comprises an alkylene glycol, the yield of ethylene glycol is significantly increased.

Accordingly, the present invention provides a process for preparing ethylene glycol from a carbohydrate source, wherein hydrogen, the carbohydrate source, a liquid diluent and a catalyst system are introduced as reactants into a reaction zone;

wherein the catalyst system comprises a tungsten compound and at least one hydrogenolysis metal selected from the groups 8, 9 or 10 of the Periodic Table of the Elements;

wherein the diluent that is introduced into the reaction zone comprises an alkylene glycol; and wherein the carbohydrate source is reacted with hydrogen in the presence of the catalyst system to yield an ethylene glycol-containing product.

DETAILED DESCRIPTION

It has surprisingly been found that the yield of ethylene glycol is increased when the diluent that is introduced in the reaction zone before the reaction is started already contains an alkylene glycol compared with a situation wherein such diluent does not comprise an alkylene glycol. This is the more surprising since during the reaction alkylene glycols are formed and the skilled person would expect that any accelerating action by the presence of an alkylene glycol would be noted in the course of the reaction. The advantage of the present invention is especially noticeable in comparison with the process of WO 2014/161852. In the process according to WO 2014/161852 a small amount of the carbohydrate source in water as diluent is added to the reactor and the yield of alkylene glycol is in the order of 25 to 40%. If such a reaction is started in the presence of an alkylene glycol, the yield of ethylene glycol alone can be well above 60%.

The carbohydrate source can be selected from a variety of sources. Suitably, the carbohydrate source contains or consists of a carbohydrate selected from the group consisting of polysaccharides, oligosaccharides, disaccharides, and monosaccharides. Suitable examples include sustainable sources such as cellulose, hemicellulose, hemicelluloses sugars, starch, sugars, such as sucrose, mannose, arabinose, glucose and mixtures thereof. Sources that may include the above carbohydrates include paper pulp streams, municipal waste water streams and other glucose units-containing streams can be used as well, for example from wood waste, paper waste, agricultural waste, municipal waste, paper, cardboard, sugar cane, sugar beet, wheat, rye, barley, other agricultural crops and combinations thereof. These streams may require pre-treatment to remove components that interfere with the present process such as basic fillers, e.g. calcium carbonate in waste paper. In this way the process according to the invention may not only be used from natural sources, but can even be used to upgrade and usefully re-use waste streams. Preferably, the carbohydrate in the carbohydrate source is selected from the group consisting of cellulose, starch, glucose, sucrose, glucose-oligomers, paper waste, and combinations thereof, preferably glucose or starch. Since cellulose presents difficulties that are absent in other carbohydrate sources, the carbohydrate source is preferably selected from the group consisting of starch, hemicellulose and hemicellulose sugars, glucose and combinations thereof.

As shown in the known processes according to the prior art, the hydrogenolysis metal can be selected from a wide range of metals. Hydrogenolysis metals may suitably be selected from the group consisting of Cu, Fe, Ni, Co, Pt, Pd, Ru, Rh, Ir, Os and combinations thereof. Preferably, the hydrogenolysis metal is selected from the noble metals Pd, Pt, Ru, Rh, Ir and combinations thereof. It has been found that these metals give good yields. The metal may suitably be present in its metallic form or as its hydride or oxide. It is assumed that the metal oxide will be reduced during the reaction in the presence of hydrogen.

The hydrogenolysis metal or the combination of hydrogenolysis metals is preferably present in the form of a catalyst supported on a carrier. The carrier may be selected from a wide range of known supports. Suitable supports include activated carbon, silica, zirconia, alumina, silica-alumina, titania, niobia, iron oxide, tin oxide, zinc oxide, silica-zirconia, zeolitic aluminosilicates, titanosilicates, magnesia, silicon carbide, clays and combinations thereof. The skilled person will know that activated carbon is an amorphous form of carbon with a surface area of at least 800 $m^2/g$. Such activated carbon thus has a porous structure. Most preferred supports are activated carbon, silica, silica-alumina and alumina, since excellent results have been obtained therewith. More preferably, the catalyst comprises ruthenium as the hydrogenolysis metal and activated carbon as the support.

Suitably, more than one metal is used in the catalyst component comprising the hydrogenolysis metal. Suitably, the combination of hydrogenolysis metals comprises at least one noble metal selected from Pd, Pt, Ru, Rh and Ir in combination with another metal from any one of the groups 8, 9 or 10 of the Periodic Table. The catalyst, preferably, comprises a mixture of two or more metals of the group consisting of Ru, Pt, Pd, Ir and Rh. Suitable examples are Ru/Ir, Ru/Pt, Ru/Pd. When two metals are used, the weight ratio is suitably in the range of 0.1:1 to 20:1. More preferably, a first hydrogenolysis metal is ruthenium and a second hydrogenolysis metal is selected from Rh, Pt, Pd and Ir. The weight ratio between Ru and the second hydrogenolysis metal is preferably in the range of 0.5:1 to 10:1.

The tungsten compound can be selected from a wide range of compounds. The tungsten may be in the elemental state. Usually, the tungsten compound is then present on a support. Similar to the supports for the at least one hydrogenolysis metal, the support may be selected from a wide range of known supports. Suitable supports include active carbon, silica, zirconia, alumina, silica-alumina, titania, niobia, iron oxide, tin oxide, zinc oxide, silica-zirconia, zeolitic aluminosilicates, titanosilicates and combinations thereof. Most preferred are activated carbon, silica, silica-alumina and alumina as support, since excellent results have been obtained therewith. It is also possible to use tungsten compounds in an oxidation state of up to +2, such as in the form of its carbide, nitride or phosphide. Also in this case the tungsten compound may be present in the form of a supported catalyst component. The carrier may be selected from the supports described hereinabove.

Preferably, the tungsten compound has an oxidation state of at least +2, preferably having an oxidation state of +5 or +6. The tungsten compound is then suitably selected from the group consisting of tungstic acid ($H_2WO_4$), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxide ($WO_3$), heteropoly compounds of tungsten, and combinations thereof. Whereas in the prior art it has been found that certain tungsten compounds leached from their supports and that such was considered a disadvantage, the present inventors have found that it is advantageous to use tungsten compounds that dissolve in the reaction mixture. It has been found that the catalytic activity of the tungsten compound increases if the tungsten compound is dissolved. Without wishing to be bound to any theory it is believed that in the reducing atmosphere that is created in the reaction zone by means of the presence of hydrogen and carbohydrates hexavalent tungsten compounds may be reduced to pentavalent tungsten and the pentavalent tungsten compound may dissolve into the diluent. In this partly reduced state the tungsten ions are effective in attacking the carbon-carbon bonds in the carbohydrate source to form alkylene glycol precursors. A preferred tungsten compound is tungstic acid. In this context it is noted that it has been found that polyols, including alkylene glycols, facilitate the dissolution of the tungsten compound into the diluent, thereby promoting the catalytic activity of the tungsten compound. The use of alkylene glycol as diluent is particularly suitable as such use does not involve the introduction of an extraneous reagent into the reaction mixture, which represents a further advantage.

According to the prior art the ratio between the at least one hydrogenolysis metal and the tungsten compound may vary between wide ranges. According to the prior art the weight ratio between these components may vary from 0.02 to 3000. In the present invention the molar ratio of tungsten to the at least one hydrogenolysis metal is preferably in the rather narrow range of 1 to 25. More preferably the molar ratio of tungsten to the at least one hydrogenolysis metal is in the range of 2 to 20, most preferably from 10 to 20. If the ratio is beyond the limits of these ranges, the relative yield of alkylene glycols other than ethylene glycol is decreased and/or the conversion of the carbohydrate is slowed down.

The concentrations of the catalyst components may vary in the process according to the present invention. The concentration of the tungsten compound may vary between very wide ranges. The concentration of the tungsten compound may for instance be selected from the range of 1 to 35% wt, calculated as tungsten and based on the weight of the carbohydrate source introduced into the reaction zone. More preferably, the amount of tungsten is in the range of 2 to 25% wt, based on the carbohydrate source introduced into the reaction zone. Since the use of relatively high amounts of tungsten does not add significant advantages to the process whereas the costs aspect may become significant, it is preferred to use amounts of tungsten of 5 to 20% wt, based on the amount of carbohydrate source.

The amount of the at least one hydrogenolysis metal selected from the groups 8, 9 or 10 of the Periodic Table of the Elements preferably ranges from 0.2 to 1.0% wt, calculated as the metal and based on the amount of carbohydrate source introduced into the reaction zone.

The carbohydrate source and the diluent are both introduced into the reaction zone. Suitably, the carbohydrate source is introduced together with at least part of the diluent. More preferably, the carbohydrate source is at least partially dissolved in the diluent. Suitably, the diluent is an aqueous medium. In the process of the present invention the diluent comprises suitably at least water and an alkylene glycol. Many carbohydrates such as sugars, glucose and fructose are soluble in water. Moreover, cellulose, i.e. a carbohydrate that is regarded as a very suitable starting material, and that is insoluble in water, can be converted into cellodextrins which are water-soluble. Alternatively, the carbohydrate may be introduced into the reaction zone in the form of a slurry. The more common examples of such slurries are aqueous mixtures of water and cellulose and/or starch. In such embodiments aqueous cellulose slurries, containing e.g. microcrystalline cellulose, can suitably be used.

The concentration of the carbohydrate source in the diluent can vary. For a commercially interesting operation higher concentrations are desirable. However, the skilled person is taught that at increasing concentration the yield of alkylene glycols will decrease. The process according to the present invention enables the skilled person to increase the concentration. Typically three modes of operation are feasible. The first mode is a batch operation in which the carbohydrate source, the diluent and the catalyst system are introduced into a reaction zone, exposed to hydrogen and reacted. In such a situation, the concentration of the carbohydrate source in the diluent is suitably from 1 to 25% wt. The diluent comprises an alkylene glycol.

A second mode is a method similar to the method according to WO 2014/161852, wherein a reaction zone is charged with the catalyst system, a diluent and a small amount of carbohydrate source, and wherein the amount of carbohydrate source is reacted with hydrogen whilst additional carbohydrate source is added with or without additional diluent. The reaction is then led to completion. The eventual amount of carbohydrate source added to the reaction zone is then suitably in the range of 10 to 35% wt, calculated as carbohydrate source based on the amount of diluent. The diluent at the start of the reaction already contains an alkylene glycol.

The third mode of operation is a continuous operation. In one continuous operation mode a feedstock comprising at least the diluent and the carbohydrate source is passed through a plug flow reactor in the presence of hydrogen and also in the presence of a catalyst system. When introduced into the plug flow reactor, the diluent contains an alkylene glycol. The concentration of the carbohydrate in the diluent may suitably be in the range of 1 to 15% wt of carbohydrate source, calculated as amount of carbohydrate source per amount of diluent. Other continuous reactors include slurry reactors and ebullating bed reactors.

A preferred embodiment of a continuous mode is to use a continuous stirred tank reactor (CSTR). The use of a CSTR is very suitable for the present process as the diluent in the CSTR provides an excellent means for diluting the eventual concentration of the carbohydrate in the CSTR, whereas the feed stream may comprise a high concentration of carbohydrate. The feed stream to the CSTR may comprise pure carbohydrate. Preferably, the feed stream is a solution or slurry of the carbohydrate in the diluent. The carbohydrate concentration in the feed stream can be rather high, since the CSTR contains a reaction medium that comprises the catalyst system, a mixture of product and carbohydrate source and diluent. During operation the CSTR is fed with one or more feed streams comprising carbohydrate source, diluent and optionally some or all of the components of the catalyst system, and from the CSTR a product stream comprising the ethylene glycol-containing product, diluent and optionally some or all of the components of the catalyst system is removed. In addition to the diluent and the carbohydrate source, also additional tungsten compound can be fed continuously or periodically to make up for any tungsten that is dissolved in the reaction mixture during the reaction, and subsequently removed from the reactor. The carbohydrate concentration in the feed stream may be rather high, and be in the range of 10 to 50% wt, calculated as amount of carbohydrate source per amount of diluent. The diluent comprises an alkylene glycol. At the same time the alkylene glycols that are produced by the reaction of the carbohydrate source provide a medium wherein tungsten compounds may be dissolved, thereby benefitting the catalytic activity of the tungsten catalyst component. The present invention therefore also provides for an embodiment wherein the present process is conducted in a CSTR wherein hydrogen, the carbohydrate source and the liquid diluent are continuously fed to the CSTR, and wherein continuously a product mixture comprising ethylene glycol and diluent is removed from the CSTR.

The process of the present invention allows for embodiments wherein high concentrations of carbohydrate source in the diluent, e.g. from 4 to 50% wt, are envisaged. The high concentration may pose problems vis-à-vis the solubility of the carbohydrate source. According to the present invention the diluent comprises an alkylene glycol. The alkylene glycol suitably has 2 to 6 carbon atoms. Suitable alkylene glycols include 1,6-hexane diol, butylene glycol and propylene glycol. However, the most preferred alkylene glycol is ethylene glycol. The diluent further typically includes water as diluent. It also functions as solvent for most of the carbohydrate sources. The amount of alkylene glycol in the diluent is suitably in the range of 2 to 25% vol, based on the volume of water and alkylene glycol. The preferred diluent is therefore a mixture of alkylene glycol, in particular ethylene glycol, and water, wherein the amount of alkylene glycol ranges from 2 to 25% vol, based on the volume of water and alkylene glycol.

In addition, the skilled person may desire to add other compounds to the diluent. Such other diluents may be selected from the group consisting of sulfoxides, alcohols other than alkylene glycols, amides and mixtures thereof. A suitable sulfoxide is dimethyl sulfoxide (DMSO); suitable examples of amides are dimethyl formamide and dimethyl acetamide. The more preferred organic diluents are the alcohols. The alcohols can be mono-alcohols, in particular water-miscible mono-alcohols, such as $C_1$-$C_4$ alcohols. The alcohol may also be a polyol, e.g. glycerol, xylytol, sorbitol or erythritol.

The prior art processes focus on the conversion of hexoses, such as cellulose, starch and glucose. However, it has been found that it is advantageous to use not only hexose-containing carbohydrates, but also pentose-containing carbohydrates. Therefore the present invention also provides a process wherein the carbohydrate source comprises at least one pentose-containing carbohydrate or, preferably, the carbohydrate source comprises a combination of at least one pentose-containing carbohydrate and at least one hexose-containing carbohydrate. The pentose-containing carbohydrate may be a polysaccharide, an oligosaccharide, a disaccharide or a monosaccharide. The pentose-containing carbohydrate is suitably a pentosan, for instance xylan or arabinan. In particular, it comprises suitably at least one of arabinose, ribose, lyxose and xylose moieties. The application of the process according to the present invention on a combination of hexose- and pentose-containing carbohydrates has the advantage that the pentose-containing carbohydrate yields both propylene glycol and ethylene glycol as main products, and the hexose-containing carbohydrates yield a majority of ethylene glycol. Hence, when propylene glycol is envisaged as a main by-product, the use of pentose-containing carbohydrate as starting material is beneficial. It is evident that the carbohydrate source that comprises hexose and pentose units may be obtained by mixing a separate hexose and a separate pentose fraction. Alternatively, the carbohydrate source may be the product of a natural source that already contains pentose and hexose units. It may e.g. be the hydrolysis product of lignocellulosic biomass, which hydrolysis results in both pentoses and hexoses.

As indicated above, the ethylene glycol-containing product of the process according to the present invention generally is a mixture of alkylene glycols. This mixture is suitably purified, especially when pure ethylene glycol is desired for polymerization purposes. The azeotrope that is formed with butylene glycol makes it difficult to obtain pure ethylene glycol.

To facilitate the separation process it is advantageous to use also pentose-containing carbohydrate as starting material. Pentose-containing carbohydrates form hardly any butylene glycol as by-product. Hence, the proportion of butylene glycol in the reaction product of a combination of pentose- and hexose-containing carbohydrates will be relatively small. The purification of such a reaction product is therefore relatively simple. Propylene glycol and ethylene glycol can be easily separated from each other by means of fractionation. Fractionation of the product of the reaction with a starting material that comprises both pentose- and hexose-containing carbohydrates will result in pure ethylene glycol, pure propylene glycol and a relatively small fraction containing butylene glycol with one or both of the other glycols.

Another method of removing butylene glycol from the products would be by using one or more entraining agents. The entraining agent selectively removes butylenes glycol from a mixture of alkylene glycols by means of azeotropic distillation. Such a procedure can be applied to processes wherein the starting material comprises only hexose-containing carbohydrates, only pentose-containing carbohydrates or a combination of both. The entraining agent can suitably be selected from the group consisting of ethyl benzene, p-xylene, n-propyl benzene, o-diethyl benzene, m-diethyl benzene, m-di-isopropyl benzene, cyclopentane, methyl cyclohexane, 3-methyl pentane, 2,3-dimethyl butane, heptane, 1-heptene, octane, 1-octene, 2,3,4-trimethyl pentane, decane, methyl ethyl ketoxime, decalin, dicyclo pentadiene, alpha-phellandrene, beta-pinene, myrcene, terpinolene, p-mentha-1,5-diene,3-carene, limonene and alpha-terpinene.

In addition, higher polyols, such as glycerol, erythritol, or sorbitol may function as an entraining agent. These compounds tend to be produced as by-products in the process for preparing ethylene glycol from carbohydrates, as shown in M. Zheng et al., Chin. J. Catal., 35 (2014) 602-613. These compounds may therefore be recycled to the process. If necessary, one or more of these compounds can also be added to the product of the present process in order to enhance their concentrations and facilitate thereby the obtaining of pure ethylene glycol, when they are used as entraining agents.

In another process for the production of pure ethylene glycol the product mixture comprising ethylene glycol, propylene glycol and butylene glycol can be converted with a carbonyl group-containing compound to form a mixture of dioxolanes. These dioxolanes do not form azeotropes and therefore can be separated relatively easily by means of distillation. After having obtained the pure dioxolanes as separate fractions, each fraction can be hydrolyzed to yield the pure corresponding alkylene glycol. The carbonyl group-containing compound suitably is an aldehyde or ketone. It preferably has a boiling point of at least 100° C., so that any water that is introduced in the reaction can be easily separated from the reaction product. Another way to enable an easy separation between water and the dioxolanes is by selecting the carbonyl group-containing compound such that at least some of the resulting dioxolanes are not soluble in water. In this way the resulting dioxolanes may be separated from water by phase separation. By doing so any water soluble by-product is also separated from the dioxolanes. One way to achieve that is by selecting a carbonyl group-containing compound that is insoluble in water itself. Very convenient carbonyl group-containing compounds include methyl isobutyl ketone, t-butyl methyl ketone and mixtures thereof. These compounds have a suitable boiling point in the range of 106 to 118° C. and they are insoluble in water. The dioxolanes formed with these compounds are also insoluble in water so that separation of these compounds from water is facilitated.

The reaction of the carbonyl group-containing compound with the alkylene glycols in the product can be catalyzed by means of a catalyst. A suitable catalyst includes an acid catalyst. Although homogeneous acid catalysts may be used, they have the drawback that the neutralization and/or separation may become cumbersome. Therefore, the acid catalyst is suitably a solid acid catalyst, preferably selected from acidic ion exchange resins, acid zeolites and combinations thereof. The use of a solid product also facilitates the contact between the liquid alkylene glycol mixture and the carbonyl group-containing compound when the dioxolane formation is carried out in a stripping column reactor, wherein a vapor of the carbonyl group containing compound is contacted in counter current with a liquid stream of the alkylene glycol mixture when this mixture is passed along the solid acid catalyst. However, it is also feasible to include a homogeneous acid catalyst in the product mixture and pass the vapor of the carbonyl group-containing compound through this liquid mixture.

When the dioxolanes have been formed they can be easily separated from each other by distillation. After distillation the separate dioxolanes can be hydrolyzed to form pure ethylene glycol. The hydrolysis of the dioxolanes is suitably also catalyzed by means of an acid catalyst. The hydrolysis may be achieved in a similar way as the formation of the dioxolanes, e.g. by counter-currently contacting a liquid stream of the dioxolane with a vaporous stream of water. The acid catalyst may be included in the dioxolane liquid or may be provided as a solid acid catalyst. The acid catalyst included in the dioxolane liquid may be a strong organic acid, such as p-toluene sulfonic acid or methane sulfonic acid. Preferably the catalyst is a solid catalyst comprising an acid ion exchange resin, an acid zeolite or a combination thereof.

The process for the preparation of ethylene glycol according to the present invention can be carried out under the process conditions that are known in the art. The conditions include those that are disclosed in WO 2014/161852. Hence, the reaction temperature is suitably at least 120° C., preferably at least 140° C., more preferably at least 150° C., most preferably at least 160° C. The temperature in the reactor is suitably at most 300° C., preferably at most 280° C., more preferably at most 270° C., even more preferably at most 250° C., and most preferably at most 200° C. The reactor may be brought to a temperature within these ranges before addition of any starting material and is maintained at a temperature within the range.

It has been found that the process according to the present invention more advantageously is carried out at temperatures that are generally somewhat lower than those used in the prior art processes. It has been found that the formation of butylene glycol is reduced if relatively low temperatures are employed. The more advantageous temperature range is from 150 to 225° C., more preferably from 160 to 200° C., and most preferably from 165 to 190° C. This is contrary to what is taught in U.S. Pat. No. 7,960,594 wherein a reaction temperature in the range 220-250° C. was stated to be most useful.

The process of the present invention takes place in the presence of hydrogen. The hydrogen can be supplied as substantially pure hydrogen. The total pressure will then be the hydrogen pressure. Alternatively, the hydrogen may be supplied in the form of a mixture of hydrogen and an inert gas. The total pressure will then consist of the partial pressures of hydrogen and this inert gas. The inert gas can suitably be selected from nitrogen, argon, neon and mixtures thereof. The ratio of hydrogen to the inert gas may vary between wide ranges. Suitably, the ratio is not very low, since the reaction proceeds well when the hydrogen partial pressure is sufficiently high. Accordingly, the volume ratio between hydrogen and the inert gas may be from 1:1 to 1:0.01. More preferably, only hydrogen is used as gas in the process according to the invention.

The pressure in the reactor is suitably at least 1 MPa, preferably at least 2 MPa, more preferably at least 3 MPa. The pressure in the reactor is suitably at most 16 MPa, more preferably at most 12 MPa, more preferably at most 10 MPa. Preferably, the reactor is pressurized by addition of hydrogen before addition of any starting material. The skilled person will understand that the pressure at 20° C. will be lower than the actual pressure at the reaction temperature. The pressure applied in the process is suitably 0.7 to 8 MPa, determined at 20° C. The pressure may be applied by hydrogen gas or a hydrogen-containing gas. When a hydrogen-containing gas is used, the hydrogen content in the hydrogen-containing gas may be up to 100 vol %, e.g. in the range of 5 to 95 vol %. The balance of the hydrogen-containing gas may suitably be an inert gas, such as nitrogen, neon, argon or mixtures thereof, as indicated hereinbefore. When the reaction mixture is subsequently heated the pressure at reaction is suitably in the range of 1 to 16 MPa. As the reaction proceeds some hydrogen is consumed. Advantageously, the hydrogen partial pressure at reaction temperature is maintained within the range of 1 to 16 MPa. It is further preferred to maintain the hydrogen pressure or hydrogen partial pressure within the range during the entire reaction. Therefore hydrogen or hydrogen-containing gas may be introduced into the reaction mixture during the reaction.

The process of the present invention may suitably be used as the first step in starting a continuous process. In such a process the reaction is started with a mixture of carbohydrate, diluent, catalyst system and hydrogen, wherein the diluent comprises an alkylene glycol. When the reaction mixture has started to react and the carbohydrate conversion has resulted in the formation of ethylene glycol, a continuous stream of carbohydrate, diluent and optionally catalyst components may be fed to the reaction zone and a continuous stream of alkylene glycol-containing product mixture may be withdrawn from the reaction zone.

Although in a batch or semi-continuous process there may not be a need for it, it is possible to add extra catalyst components such as tungsten compound or the hydrogenolysis metal to the reaction mixture during the course of the reaction. Such may be found desirable when the reaction is prolonged and the concentration of the catalyst system gets below a desired level, due to the addition of diluent and/or carbohydrate.

The reaction time in the process according to the present invention may vary. Suitably the residence time of the carbohydrate source is at least 1 min. Preferably the residence time is in the range of 5 min to 6 hrs, more preferably from 5 min to 2 hr. In a batch process the residence time is the time during which the carbohydrate source is contacted with hydrogen and the catalyst system under reaction conditions. In a continuous process the residence time is understood to be the quotient of the mass flow rate of the carbohydrate source into the reaction zone divided by the mass flow rate of the catalyst system in the reaction zone. In general a continuous process is operated at a weight hourly space velocity (WHSV), expressed as the mass of carbohydrate source per mass of hydrogenolysis metal, expressed as metal, per hour, in the range of 0.01 to 100 $hr^{-1}$, preferably from 0.05 to 10 hr'.

The invention will be further illustrated by means of the following Examples.

EXAMPLE

In a series of experiments ruthenium on activated carbon (5% wt Ru on C) as hydrogenolysis catalyst component and tungstic acid ($H_2WO_4$) as tungsten compound were added to a reaction vessel in such amounts that the amount of ruthenium was 12.5 mg and the amount of tungstic acid was 500 mg. The molar ratio of tungsten to ruthenium, calculated as metal/metal, was 16.2 in all experiments. An amount of 40 ml of diluent was added; in experiments according to the invention the diluent contained ethylene glycol in certain amounts and water. The diluent in comparative experiments consisted of water only. The reactor was subsequently pressurized with 50 bar hydrogen and then heated to the desired reaction temperature in the range of 180 to 210° C.

When the reactor was at the desired temperature, a feed solution of 50 g glucose in 100 ml water was pumped into the reaction vessel at a rate of 0.1 ml/min. The feed solution was added for 50 or 100 min. Thereafter the pressure was released and the temperature decreased. The resulting product was analyzed for the amount of ethylene glycol and butylene glycol. When determining the amount of ethylene glycol, the yield of ethylene glycol was calculated as the total amount of ethylene glycol in the reaction mixture minus the amount of ethylene glycol added in the diluent.

The table below shows the experiment number, the percentage of ethylene glycol in the diluent ("dil EG"), expressed in vol %, the amount of tungstic acid (in mg) ("$H_2WO_4$"), the molar ratio of tungsten to ruthenium ("W/Ru"), the reaction temperature ("T") in ° C., time ("t") in minutes during which the feed rate was continued, the yield on ethylene glycol ("y EG"), yield on propylene glycol ("y PG") and the yield on butylene glycol ("y BG"), all calculated as the percentage of grams obtained divided by the amount of grams glucose as starting material.

TABLE

| Exp. No. | dil EG, vol% | T, ° C. | t, min | yEG, % wt | yPG, % wt | yBG, % wt |
|---|---|---|---|---|---|---|
| 1 | 16.8 | 180 | 50 | 72.5 | 0.3 | 0.0 |
| 2 | 4.1 | 180 | 50 | 55.3 | 1.1 | 0.0 |
| 3 | 4.1 | 190 | 50 | 52.4 | 1.2 | 0.5 |
| 4 | 3.7 | 200 | 100 | 66.4 | 3.0 | 2.5 |
| 5 | 15.2 | 180 | 100 | 64.9 | 0.7 | 0.1 |
| 6 | 7.5 | 200 | 100 | 64.4 | 1.3 | 0.0 |
| 7 | 0 | 190 | 100 | 39.3 | 2.0 | 0.6 |
| 8 | 0 | 200 | 50 | 33.3 | 1.2 | 0.1 |
| 9 | 0 | 210 | 50 | 25.7 | 1.1 | 0.0 |
| 10 | 0 | 190 | 100 | 25.7 | 0.9 | 0.6 |

The results of the above experiments show that the yield of ethylene glycol is increased when the diluent contains a percentage of ethylene glycol at the start of the reaction. Surprisingly, the selectivity towards ethylene glycol increases as the yields of propylene glycol and butylene glycol are similar both in the experiments according to the invention (Exp. Nos. 1-6) and in the comparative experiments (Exp. Nos. 7-10).

The invention claimed is:
1. Process for preparing ethylene glycol from a carbohydrate source,
   wherein hydrogen, the carbohydrate source, a liquid diluent and a catalyst system are introduced as reactants into a reaction zone;
   wherein the catalyst system comprises a tungsten compound and at least one hydrogenolysis metal selected from the groups 8, 9 or 10 of the Periodic Table of the Elements;
   wherein the diluent that is introduced into the reaction zone comprises an alkylene glycol; and
   wherein the carbohydrate source is reacted with hydrogen in the presence of the catalyst system to yield an ethylene glycol-containing product.
2. Process according to claim 1, wherein the diluent comprises ethylene glycol.
3. Process according to claim 1, wherein the carbohydrate source is selected from the group consisting of polysaccharides, oligosaccharides, disaccharides, and monosaccharides.

4. Process according to claim 1, wherein the carbohydrate source is selected from the group consisting of cellulose, starch, hemicellulose, hemicellulose sugars, glucose and combinations thereof.

5. Process according to claim 1, wherein the catalyst system comprises a tungsten compound that has an oxidation state of at least +2.

6. Process according to claim 1, wherein the catalyst system comprises a tungsten compound selected from the group consisting of tungstic acid ($H_2WO_4$), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxide ($WO_3$), heteropoly compounds of tungsten, and combinations thereof.

7. Process according to claim 6, wherein the catalyst system comprises tungstic acid.

8. Process according to claim 1, wherein the hydrogenolysis metal from groups 8, 9 or 10 of the Periodic Table of the Elements is selected from the group consisting of Cu, Fe, Ni, Co, Pd, Pt, Ru, Rh, Ir, Os and combinations thereof.

9. Process according to claim 1, wherein the at least one hydrogenolysis metal from the groups 8, 9 or 10 of the Periodic Table of the Elements is present in the form of a catalyst supported on a carrier.

10. Process according to claim 9, wherein the carrier is selected from the group supports, consisting of activated carbon, silica, alumina, silica-alumina, zirconia, titania, niobia, iron oxide, tin oxide, zinc oxide, silica-zirconia, zeolitic aluminosilicates, titanosilicates, magnesia, silicon carbide, clays and combinations thereof.

11. Process according to claim 8, wherein the catalyst system comprises ruthenium on activated carbon.

12. Process according to claim 1, wherein the molar ratio of tungsten to the at least one hydrogenolysis metal is in the range of 1 to 25.

13. Process according to claim 1, wherein the concentration of the tungsten compound is in the range of 1 to 35% by wt, calculated as tungsten and based on the weight of the carbohydrate source.

14. Process according to claim 1, wherein the amount of the at least one hydrogenolysis metal selected from the groups 8, 9 or 10 of the Periodic Table of the Elements ranges from 0.2 to 1.0% by wt, calculated as the metal and based on the amount of carbohydrate source introduced into the reaction zone.

15. Process according to claim 1, wherein the carbohydrate source comprises a combination of at least one pentose-containing carbohydrate and at least one hexose-containing carbohydrate.

16. Process according to claim 1, wherein the diluent is a mixture of alkylene glycol and water, wherein the amount of alkylene glycol ranges from 2 to 25% by vol, based on the volume of water and alkylene glycol.

17. Process according to claim 16, wherein the diluent further comprises one or more compounds selected from the group consisting of sulfoxides, alcohols other than alkylene glycols, amides and mixtures thereof.

18. Process according to claim 17, wherein the diluent is glycerol, xylytol, sorbitol or erythritol.

19. Process according to claim 1, wherein the ethylene glycol-containing product is purified.

20. Process according to claim 19, wherein the ethylene-glycol-containing product is purified by using one or more entraining agents.

21. Process according to claim 1, wherein the temperature in the reaction zone ranges from 120 to 300° C.

22. Process according to claim 1, wherein a hydrogen partial pressure in the reaction zone is in the range of 1 to 6 MPa.

23. Process according to claim 1, wherein the average residence time of the catalyst system in the reaction zone is in the range of 5 min to 6 hrs.

24. Process according to claim 1, wherein a diluent already containing an alkylene glycol is introduced in the reaction zone before a reaction of the carbohydrate source with hydrogen in the presence of the catalyst system to yield an ethylene glycol-containing product is started in such reaction zone.

25. Continuous process comprising a first step starting the continuous process,
wherein the first step comprises a process for preparing ethylene glycol from a carbohydrate source, wherein hydrogen, the carbohydrate source, a liquid diluent and a catalyst system are introduced as reactants into a reaction zone; wherein the catalyst system comprises a tungsten compound and at least one hydrogenolysis metal selected from the groups 8, 9 or 10 of the Periodic Table of the Elements; wherein the diluent that is introduced into the reaction zone comprises an alkylene glycol; and wherein the carbohydrate source is reacted in a reaction with hydrogen in the presence of the catalyst system to yield an ethylene glycol-containing product; and
wherein the reaction is started with a mixture of carbohydrate, diluent, catalyst system and hydrogen, wherein the diluent comprises an alkylene glycol.

* * * * *